United States Patent
Chou

(10) Patent No.: US 8,939,149 B2
(45) Date of Patent: Jan. 27, 2015

(54) AIR DELIVERY SYSTEM

(75) Inventor: Chang-An Chou, Taipei (TW)

(73) Assignee: MD Biomedical, Inc., Taipei (TW)

( * ) Notice: Subject to any disclaimer, the term of this patent is extended or adjusted under 35 U.S.C. 154(b) by 395 days.

(21) Appl. No.: 13/519,322

(22) PCT Filed: Dec. 28, 2010

(86) PCT No.: PCT/CN2010/002184
§ 371 (c)(1),
(2), (4) Date: Jun. 27, 2012

(87) PCT Pub. No.: WO2011/079521
PCT Pub. Date: Jul. 7, 2011

(65) Prior Publication Data
US 2012/0318266 A1   Dec. 20, 2012

(30) Foreign Application Priority Data

Dec. 28, 2009   (CN) .......................... 2009 1 0312425

(51) Int. Cl.
A61M 11/00   (2006.01)
A61B 5/087   (2006.01)
A61B 16/00   (2006.01)
A61B 5/00    (2006.01)
A61M 16/00   (2006.01)

(52) U.S. Cl.
CPC .................. *A61B 5/087* (2013.01); *A61B 16/00* (2013.01); *A61B 5/4818* (2013.01); *A61M 2016/0021* (2013.01); *A61M 2016/0036* (2013.01); *A61M 2205/15* (2013.01)

USPC .................................. 128/204.23; 128/204.21

(58) Field of Classification Search
USPC ............................ 128/204.18, 204.21, 204.23
See application file for complete search history.

(56) References Cited

U.S. PATENT DOCUMENTS

| 6,305,372 | B1 | 10/2001 | Servidio |
| 7,814,907 | B2* | 10/2010 | Bremner et al. ......... 128/205.23 |
| 2007/0193583 | A1 | 8/2007 | Reed |
| 2010/0175699 | A1* | 7/2010 | Varney et al. ............ 128/204.23 |

FOREIGN PATENT DOCUMENTS

| CN | 1440302 | 9/2003 |
| CN | 1764486 | 4/2006 |
| CN | 101106941 | 1/2008 |
| CN | 101618247 | 1/2010 |
| EP | 0798005 | 10/1997 |

* cited by examiner

*Primary Examiner* — Steven Douglas

(57) ABSTRACT

An air delivery system is provided. The air delivery system includes a PAP device having a flow generator, a patient interface, a processor and a connector, and at least a removable sensing device having at least a sensor, a front-end analog circuit and a connector. The sensor is integrated with the patient interface to measure a respiratory characteristic in a path between the patient's upper airway and the flow generator. When the removable sensing device is separated from the PAP device, the PAP device enters a first operation mode to perform a first preset air delivery behavior, and when the removable sensing device is coupled to the PAP device through the connectors respectively thereof, the PAP device enters a second operation mode to perform a second air delivery behavior for adjusting the treatment pressure in accordance with the respiratory characteristic.

15 Claims, 4 Drawing Sheets

AIR DELIVERY SYSTEM

FIELD OF THE INVENTION

The present invention is related to an air delivery system for treating sleep related breathing disorders, and more particularly to an air delivery system which can be integrated with an external device to alter the hardware arrangement thereof, thereby varying an air delivery behavior at the same time.

BACKGROUND OF THE INVENTION

Obstructive sleep apnea syndrome (OSAS) is a cessation of oronasal airflow caused by narrowed or collapsed upper airway.

The most commonly prescribed treatment for obstructive sleep apnea is to provide a continuous positive airway pressure during the sleep. A positive airway pressure device (PAP device) delivers air pressure through a nasal/oralnasal mask that the patient wears while sleeping. The pressure keeps the throat open for eliminating obstructive apneas and allowing the patient to breathe normally for whole night and to keep sleep uninterruptedly and restoratively.

One common type of PAP devices is CPAP device which provides a constant air delivery pressure. Other types of PAP devices are also available. For example, one is BiPAP (Bilevel PAP) device which provides two positive pressures, a lower pressure for the patient's expiration and a higher pressure for the inspiration. Another one is APAP (Auto PAP) device which automatically detects the patient's apnea/hypopnea and alters the air pressure according thereto. A further one is VPAP (Variable PAP) device which adjusts the air pressure in accordance with the patient's breathing pattern automatically.

All these developments are focused on adjusting the air pressure based on the patient's breathe, and thus, preventing improper air delivery pressure. Insufficient delivery pressure might be unable to open the airway, and excess delivery pressure might bring the patient uncomfortability, and also, cause mask leakage and/or arousal which on the contrary will influence the patient's sleep. Therefore, how to find out the minimum effective delivery pressure for the patient's most comfortability is one of the main goals in PAP development, and an example can be seen in U.S. Pat. No. 6,349,724.

However, as known, most PAP devices have a fixed hardware structure which limits the adaptation to the patient's different demands. Some improvements for this limitation are US 2007/0193583, which increases preloaded programs to provide multiple delivery modes, and US 2007/0023045, which provides the possibility to alter the hardware, and further, U.S. Pat. No. 6,397,845 and U.S. Pat. No. 7,204,250 provide the information about sleep stage according to the physiological signals for being the basis of air pressure adjustment.

The object of the present invention is to provide an air delivery system with hardware flexibility.

Another object of the present invention is to provide an air delivery system in which a PAP device can obtain additional functions through connecting with at least an external sensing device.

A further object of the present invention is to provide an air delivery system which employs an external and removable sensing device to provide signal inputs to the PAP device for adjusting the air delivery pressure to match the patient's real need.

Another further object of the present invention is to provide a multifunctional air delivery system in which the PAP device can cooperate with the external/removable sensing device or can operate independently.

SUMMARY OF THE INVENTION

As described above, the improvements of PAP device are mainly focused on optimizing the delivery pressure to maximize the comfortability and reduce the influences caused by improper delivery pressure.

In one aspect of the present invention, it provides an air delivery system including a PAP device and at least a removable sensing device. The PAP device includes a flow generator for providing breathable gas at a pressure elevated above atmosphere, a patient interface having a gas delivery tube coupled to the flow generator and a patient mask coupled to the gas delivery tube to receive breathable gas from the flow generator and to provide the gas, at a desired treatment pressure, to a patient's airway, a processor for controlling a magnitude of the treatment pressure provided by the flow generator, and a connector electrically connected to the removable sensing device. The removable sensing device includes at least a sensor capable of being integrated with the patient interface to measure a respiratory characteristic in a path between the patient's upper airway and the flow generator, a front-end analog circuit for processing the measurements from the sensor to generate signal inputs to the processor, and a connector electrically connected to the PAP device. During operation, if the removable sensing device is separated from the PAP device, the PAP device enters a first operation mode, in which a preloaded program in the processor performs a first preset air delivery behavior to control the treatment pressure, and if the removable sensing device is connected to the PAP device through the connectors respectively thereof, the PAP device enters a second operation mode, in which the preloaded program performs a second air delivery behavior for adjusting the treatment pressure in accordance with the respiratory characteristic from the signal inputs.

In the second operation mode, the preload program, based on different settings stored therein (such as, automatically or via the selection from the patient), will decide the processing procedure for the signal inputs. For example, the signal inputs can be used as the primary or secondary basis for pressure regulation or even be omitted, without limitation. The only purpose is to provide the patient an optimized treatment pressure.

The front end analog circuit is implemented to provide functions of signal filtering, level shifting and/or signal amplification before the signals are inputted into the PAP device, and the removable sensing device can further include an analog to digital converter for digitizing the signals and thus improving transmission stability.

Here, the respiratory characteristic includes, but not limited, one or more selected from a group consisting of the occurrence of sleep apnea/hypopnea, the duration of sleep apnea/hypopnea, the waveform contour of expiration, and the waveform contour of inspiration. Through detecting the respiratory characteristic of the patient, it can realize how to regulate the air pressure, such as, to increase, decrease or remain the current treatment pressure. For example, during the expiration period, a lower delivery pressure can reduce the occurrence of arousal, and a higher pressure during the inspiration period can prevent insufficient air delivery.

Preferably, the sensor can be, but not limited, a flow sensor or a thermal sensor, or any other sensor which can be used to measure the respiratory characteristic. Here, the sensor can be positioned on the vent hole(s) of the mask, inside the mask, or on the gas delivery tube, or can be connected between the gas delivery tube and the PAP device or connected to the PAP device through another tube, or located at any position capable of measuring the respiratory characteristic, without limitation.

Further, the numbers and the types of both the sensing device and the sensor are also not restricted. It can be plural sensing devices connected to the PAP device, and/or plural sensors connected to the sensing device, which is depending on the patient's requirement.

According to another aspect of the present invention, the sensor contained in the removable sensing device also can be implemented to be a pressure sensor integrated with the patient interface, so as to measure a pressure characteristic in the path between the patient's upper airway and the flow generator, and the processor can regulate the delivery pressure in accordance with this pressure characteristic during the second operation mode.

The pressure characteristic can be used to decide if the pressure at the pressure interface is higher or lower than preset values, if there exists any special pressure variation, and/or the duration of pressure variation, and thus, the system can figure out, for example, if the mask is worn on or taken off, or if there is any leakage from the worn mask, so as to have a corresponding response, for example, to turn on/off the air delivery or to notify/record the mask leakage.

In a preferred embodiment, the pressure sensor also can be used to detect the atmospheric pressure, so that the system can accordingly have a pressure adjustment based on the elevation.

Furthermore, the air delivery system according to the present invention also can utilize two more sensors to provide single regulation basis, such as, to measure the respiratory and the pressure characteristics together, so as to satisfy the patient's real demands more.

Therefore, through the removable sensing device, the present invention provides the patient, in a cost effective way, the possibility to alter the hardware of the air delivery system to response to the demand variation, for example, when there appears different physical conditions (e,g., healthy or catching a cold) or purposes (e.g., for travelling or home usage). Moreover, the removable sensing device also provides the patient the option to decide the function of the PAP device, which therefore enhances a customized treatment.

BRIEF DESCRIPTION OF THE DRAWINGS

A more detailed understanding of the invention may be had from the following description of a preferred embodiment, given by way of example, and to be understood in conjunction with the accompanying drawings, wherein.

DETAILED DESCRIPTION OF THE PREFERRED EMBODIMENTS

According to the concept of the present invention, the air delivery system includes two portions: a PAP device and at least a removable sensing device. The PAP device is used to provide a breathable pressured air to the patient which can operate independently or with the removable sensing device. The removable sensing device is connected with the PAP device for providing signal inputs as the basis of pressure regulation/adjustment.

Figure 1:
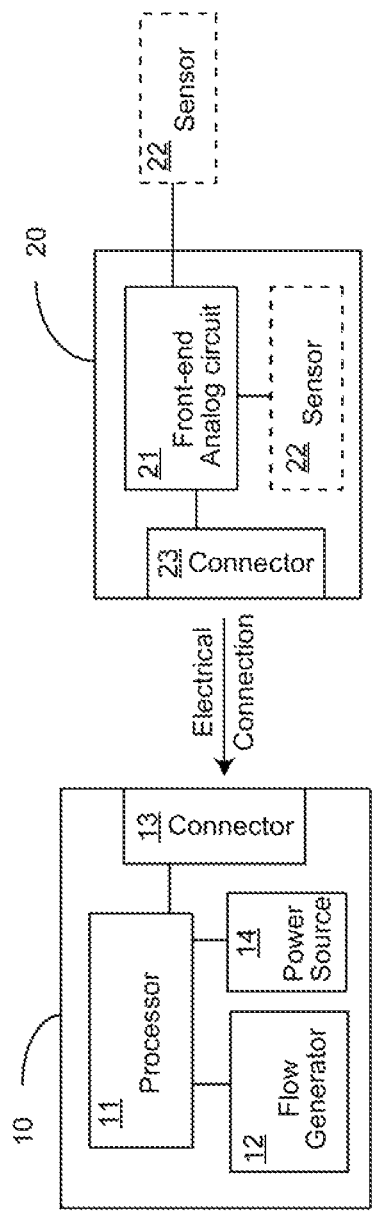
FIG. 1 is a block showing the PAP device and the removable sensing device according to the present invention
Figure 2:
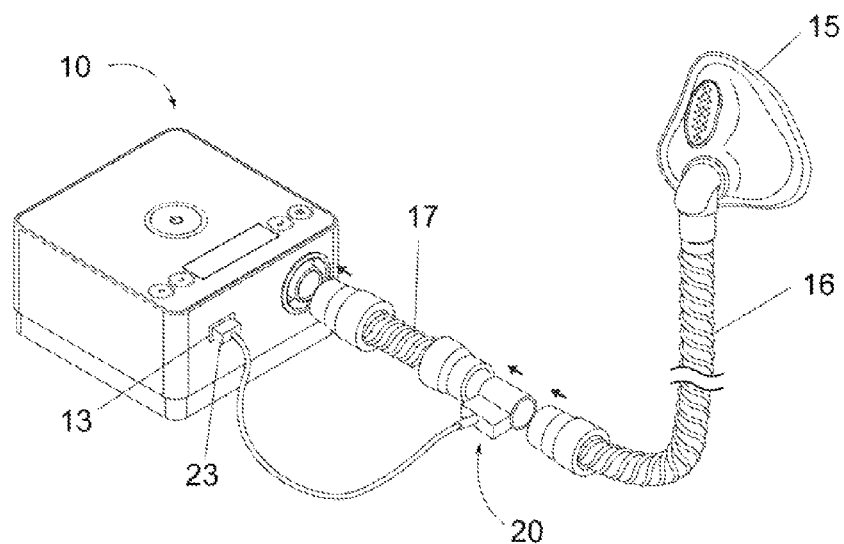
FIG. 2 is a schematic view showing the PAP device and the removable sensing device in a preferred embodiment of the present invention.

Please refer to FIG. 1 which is a block showing the PAP device and the removable sensing device according to the present invention, and FIG. 2 which shows the PAP device and the removable sensing device in a preferred embodiment of the present invention. As shown, the PAP device 10 of the present invention includes a processor 11, a flow generator 12, a connector 13 and a power source 14, wherein the processor 11 has a preloaded program for controlling the PAP device 10, the flow generator 12 supplies a breathable air of therapeutic pressure to the patient according to an indication from the processor 11, the connector 13 is used to connect to the removable sensing device 20, and the power source 14 provides electricity for operation. Here, if the PAP device is used at home, the wall outlet is usually employed as the power source, and if the PAP device is used as traveling, the battery can be used as the power source, but there is no limitation.

Of course, for supplying breathable pressured air to the patient, the PAP device 10 also should be connected to a patient interface, such as a mask 15, a gas delivery tube 16 and other related accessories (as shown in FIG. 2), for ensuring the air delivery to the patient's upper airway. However, since the patient interface is well known in the art, it is omitted in the following descriptions.

Furthermore, the external sensing device 20 includes a front-end analog circuit 21, at least a sensor 22, and a connector 23. As shown in FIG. 2, after the removable sensing device 20 and the PAP device 10 are connected together through the respective connectors 13, 23, the sensing device 20 can be controlled by the processor 11 in the PAP device 10, so that according to the indication from the processor 11, the sensing device 20 measures a characteristic in an air delivery path between the patient's upper airway and the flow generator, such as, flow rate, and pressure. Here, as shown in FIG. 1, the sensor 22 can be built in or externally connected to the sensing device 20, depending on the real situation, without limitation. In addition, the connectors 13, 23 can be, but not limited, any wired connection interface, such as, USB connectors, serial ports, RJ45.

According to the present invention, the sensor 22 can be used to measure a respiratory characteristic in the air delivery path, for example, the respiratory cycle, the waveform contours of inspiration/expiration, the occurrence of sleep apnea/hypopnea, and the duration of sleep apnea/hypopnea. The respiratory characteristic, no matter is obtained directly or indirectly, can be used as the reference for adjusting the treatment pressure, such as, for providing a proper ramp period before the patient falls asleep, for decreasing the pressure during expiration, for increasing the pressure during inspiration, and for remaining a pressure which keeps from the occurrence of sleep apnea and makes the patient feels comfortable, namely, for obtaining a profile of minimum effective pressure during sleep so as to maximize the comfortability.

The sensor 22 includes, but not limited, thermal sensor (such as, thermistor, thermal coupler etc.), flow sensor (such as, flowmeter, pressure sensor etc.) and any other sensor capable of measuring the respiratory characteristic in the air delivery path. The sensor 22 can be mounted within the air delivery path at different positions in accordance with the type thereof. For example, as shown in FIG. 2, the sensing device 20 utilizes a built-in sensor to measure the respiratory characteristic, and another short gas delivery tube 17 is used for connecting the sensing device 20 between the PAP device 10 and the tube 16 and the mask 15. In this case, it will be more suitable for adopting a flowmeter. However, there is no limitation. Then, after the connector 23 and the connector 13 are connected together, as usual, the patient can operate the PAP device and fall asleep with no difference, but the PAP device, owing to the external connection, has already upgraded to provide additional function(s). Therefore, the patient can obtain more choices with the same PAP device.

Figure 3A:
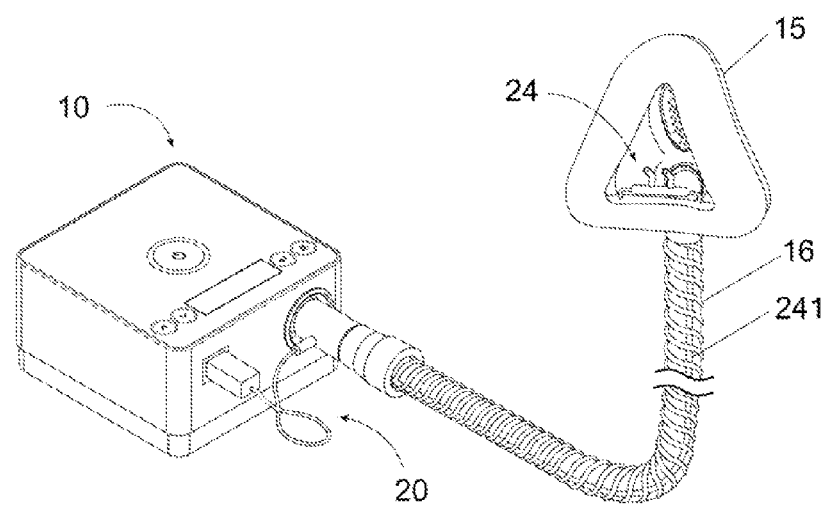
FIGS. 3A to 3C are schematic views showing the PAP device and the removable sensing device in different preferred embodiments of the present invention.
Figure 3B:
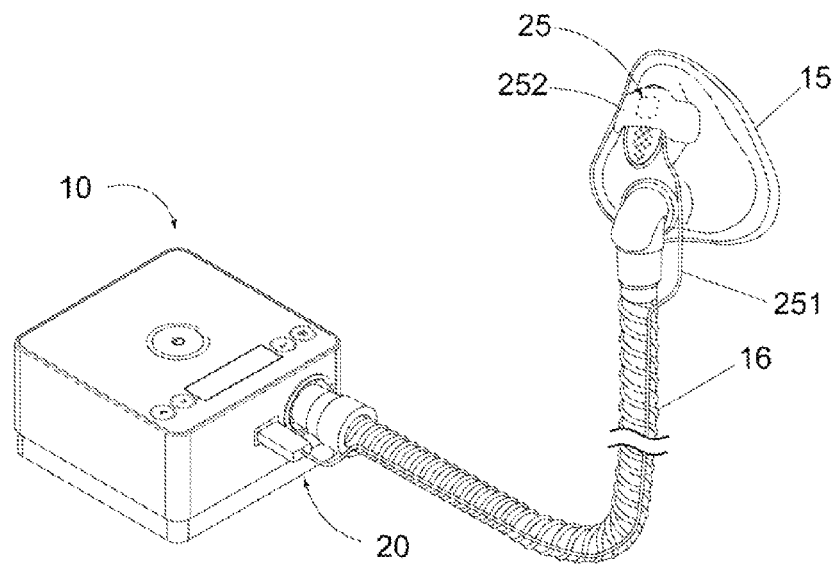
Figure 3C:
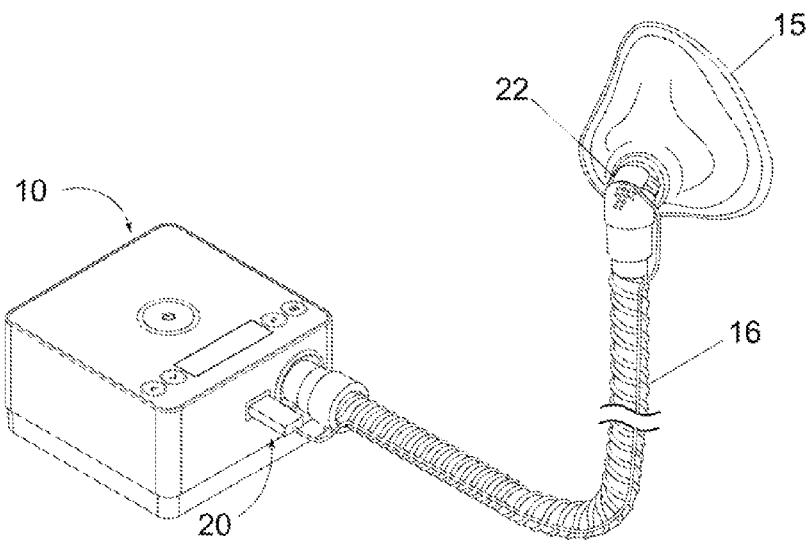

Moreover, please refer to FIG. 3A to FIG. 3C, which exemplarily illustrate external sensors and the arrangements thereof. As shown in FIG. 3A to FIG. 3B, a airflow sensor 24 or a thermstor 25 can be mounted between the nose and the mouth or on the vent hole(s) of the mask. When the sensor is implemented to directly integrate with the structure of the mask, such as, a thermistor or flow tube (FIG. 3A), an air conducting tube 241 or a connecting line 251 can be positioned inside the air delivery tube 16. When the sensor is implemented to put on the vent holes 151, as shown in FIG. 3B and FIG. 3C, the air conducting tube 241 or the connecting line 251 can just stay close to the outer surface of the tube 16. Here, FIG. 3B and FIG. 3C respectively show different manners for the sensor to combine with the vent holes 151, in FIG. 3B, a patch 252 is employed, and in FIG. 3C, the sensor is hooked on the mask.

One skilled in the art can understand that the sensors described above and the arrangements thereof are only for illustration, and other sensors and arrangements are also possible, without limitation. The main goal is to obtain the information about respiration and provide the patient the convenience.

According to another aspect of the present invention, the sensor 22 of the removable sensing device 20 also can be used to measure a pressure characteristic in the air delivery path, such as, through a pressure sensor, for being the reference to control the delivery pressure. Through this manner, it can further reveal that if the patient breaths to the mask or not, or if the mask has any leakage. As to the arrangement of the pressure sensor, it is similar to the situations described above and is omitted for simplification.

The pressure sensor can be used to determine when to turn on the air delivery. For example, when the air delivery is not yet started, if the patient uses the mask to cover the nose (and the mouth) and starts to breath into the mask, then a regular fluctuate of pressure can be observed in the air delivery path due to the inspiration and expiration. After the pressure sensor detects several times of fluctuate (such as, two to three times), it can decide that the patient is trying to start the treatment, thereby the system can turn on the air delivery. On the other hand, the pressure sensor also can be used to decide when to turn off the air delivery. For example, when the mask is moved away from the patient's face, the pressure in the air delivery path will have a dramatic drop and last for a period of time, so that according to this, the system can turn off the air delivery automatically.

Besides, through detecting the pressure characteristic, the leakage of mask also can be revealed. Generally, there are two causes of leakage: one is the unfitness of mask, and the other is the body movement during treatment.

For the first situation, it can be set to detect, at the beginning of treatment, if there is a preset pressure drop between the therapeutic pressure and the measured pressure, which represents the patient does not fit the mask well, and then, the system can warn the patient this situation until a proper fitness is achieved.

For the second situation, a pressure drop range during the treatment can be specified to represent the position shifting of the mask. And, since the patient might be sleeping, the warning can be short, and a record of this situation can be stored (such as, in the memory) for further notification after treatment, such as, through the display. Therefore, the patient can pay more attention to mask fitness and/or body position during treatment. Also, the record(s) can provide the doctor the information for diagnosis.

It also can be implemented to detect the respiratory characteristic and the pressure characteristic at the same time, for example, to adapt two sensors, so as to regulate the pressure more detailedly. It should be noted that the measurement principles of two sensors can be identical or different, without limitation.

Based on the property of the sensor, the pressure sensor also can be used to detect the atmosphere pressure around the PAP device, so as to regulate the delivery pressure in accordance with the elevation at which the PAP device is located. In a preferred embodiment, the pressure sensor is used to detect the respiratory characteristic and the atmosphere pressure at the same time, and in this case, the sensor should be located in the air delivery path, such as, on the mask or tube. In another preferred embodiment, the pressure sensor also can be implemented to detect the atmosphere pressure only, so that the position of the sensor only needs to be close to the PAP device and/or the patient, and is not limited to be located on the mask/tube.

It should be noted that the embodiments described above are only for illustration and not for limitation. And, other methods derived from the embodiments described above for regulating the delivery pressure based on the detected pressure characteristic are also obvious for those skilled in the art.

Particularly, different from a common PAP device, the sensing device 20 of the present invention is implemented to be removable, so that the user, according to the real demand, can change or replace the sensing device 20, or select to connect or not connect with the sensing device 20. Generally, the PAP device has fixed function(s) which is difficult in changing, so that the decision before purchase is necessary. However, the physical condition of human beings might be varied with time, such as, to gain weight, lose weight or have a stuffy nose, so as to make the original selection improper. Therefore, the removable manner of the present invention provides the user the opportunity to alter the hardware and function in addition to replacing the whole device.

Moreover, owing to the type of external connection, the additional circuits for processing different kinds of physiological signals can be directly mounted in each removable sensing device, so that not only the signals can be processed properly without being limited by the given circuitry in the PAP device, but the cost and volume of the PAP device can be minimized since the need to encompass the circuits for all possible kinds of physiological signals is eliminated.

Thus, according to the present invention, the removable sensing device can include the front-end analog circuit 21 for processing the measurements, including, but not limited, filtering (e.g., low pass filtering, high pass filtering, or notch filtering), amplification, and level shifting, so as to generate signal inputs to the PAP device. The removable sensing device 20 also can include an analog to digital converter for digitizing the signals before entering to the PAP device 10. The prior processing provides more stable signal transmission and benefits the process and analysis in the PAP device.

Because the removable sensing device is implemented to employ an external connection, the PAP device only needs to be capable of receiving the signal inputs, and the type thereof is not restrictive. That is, in addition to the basic CPAP device, the PAP device also can be originally equipped with the function of pressure regulation/adjustment, such as, a BiPAP or AutoPAP. In this case, the signal inputs from the sensing device may become an additional basis, so as to provide a more precise pressure regulation.

Followings describe the operation of the PAP device 10 and the removable sensing device 20.

Figure 4:
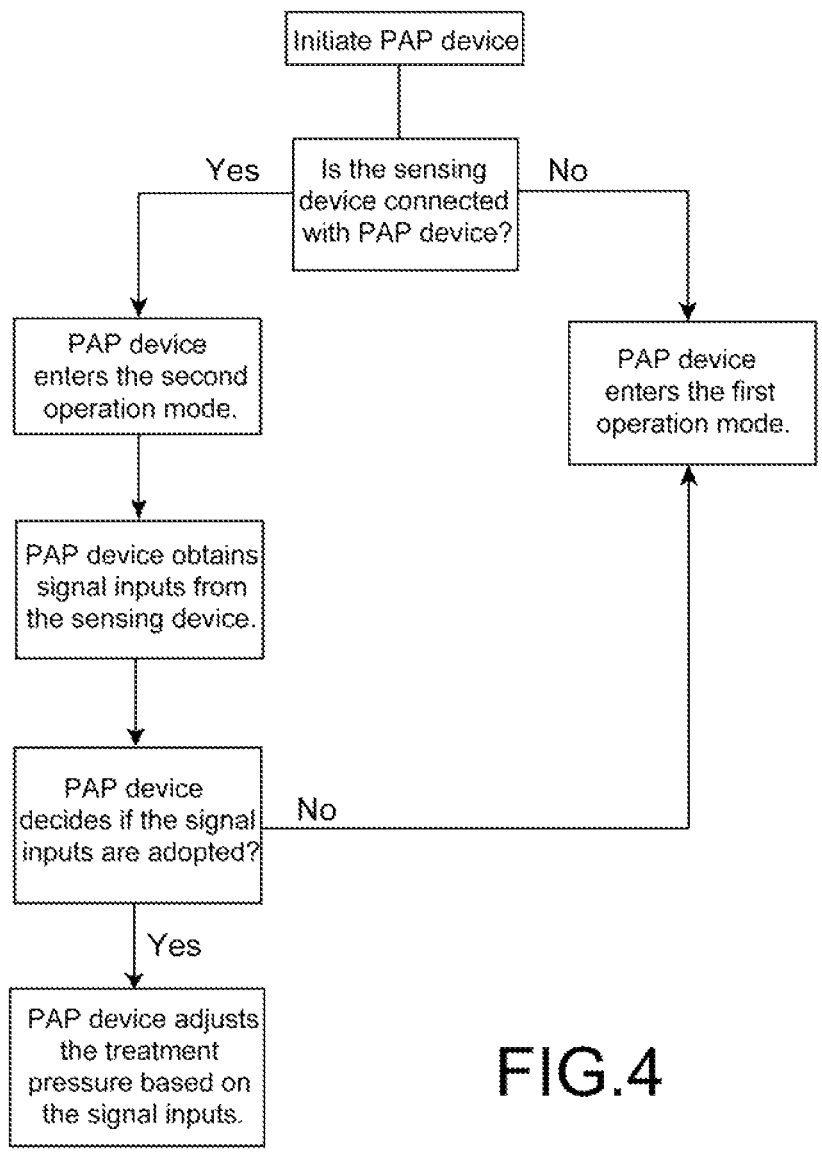
FIG. 4 is a flow chart showing the operation of the air delivery system according to the present invention.

As shown in FIG. 4, which is a flow chart showing the operation of the air delivery system according to the present invention. First, after the PAP device 10 is turned on, the processor 11 will check if the removable sensing device 20 is connected therewith.

1. If There is No External Connection Found:

The PAP device 10 operates independently, and enters a first preset operation mode, in which the preloaded program in the processor 11 performs a first air delivery behavior for delivering a preset therapeutic pressure. Here, if the PAP device 10 is a CPAP device, the air delivery behavior will be delivering a breathable air having a fixed pressure, or if the PAP device 10 is a BiPAP device, the air delivery behavior will be delivering a breathable air varying between two pressures. Therefore, the original functions of the PAP device 10 will not be influenced.

2. If There Finds a Connection from the Removable Sensing Device 20:

The PAP device 10 enters a second operation mode and works with the sensing device 20, in which the preloaded program in the processor 11 performs a second air delivery behavior for regulating the delivery pressure based on the signal inputs from the sensing device 20.

Particularly, when the removable sensing device 20 and the PAP device 10 are connected through the respective connectors 13, 23 thereof, in addition to the signal inputs related to respiratory/pressure characteristic, other signals also can be inputted, such as, identification signals for distinguishing the type, the model and/or the status of the sensing device 22/sensor 20. And, through this connection, the PAP device can output a control signal to control the behavior (such as, turning on/off) of the sensing device 20/sensor 20. Further, the connection therebetween also can achieve other purposes, such as, power supply, without limitation. Besides, the signal transmission therebetween can be digital or analog.

When the removable sensing device 20 is connected, a checking process will first be performed by the PAP device, for example, it can be implemented that the PAP device automatically identifies the type/model of the sensing device/sensor, or the doctor/technician/patient manually inputs/selects the type/model. Alternatively, it also can combine the methods described above, for example, it can be the type/model is manually inputted first, and then, the PAP device automatically performs the identification, without limitation. Here, through checking the type/model of the sensing device/sensor, the PAP device can learn the signal inputs.

Then, the PAP device adjusts the therapeutic pressure based on the received signal inputs. As to how the signal inputs involve the pressure regulation, it can be decided automatically by the program, or manually. For example, the PAP device can be set (e.g., by the doctor/technician), in accordance with the patient's physical condition, to receive or not receive the signal inputs, to receive which type of signal inputs, and/or to receive the signal inputs at a specified condition. Another situation is a built-in program is employed to make a better decision for the patient. For example, if the PAP device is a BiPAP device, which originally has the capability to detect the pressure difference between the inspiration and expiration, the program can decide if the additional signal inputs are helpful or not, and if not, then the BiPAP device can omit the signal inputs from the sensing device. Alternatively, if the signal inputs provide a better regulation basis, the PAP device can employ the signal inputs to replace the original one. Alternatively, the BiPAP device can employ both bases to decide an optimal therapeutic pressure. Therefore, there is no limitation to the role of the signal inputs from the sensing device, and the primary goal is to obtain a pressure close to the patient's real need.

After the decision, the processor 11 controls the flow generator to adjust the delivered pressure, such as, to increase, decrease or remain the pressure. During the whole treatment, the checking, deciding and adjusting processes are constantly repeated to seek an optimal pressure.

Consequently, through the design of the present invention, any kind of PAP device can obtain an additional pressure regulation function by connecting with a removable sensing device.

For example, if the PAP device is originally a CPAP device which delivers constant pressure, by connecting with different sensing devices, the CPAP device can be provided with additional capabilities for air delivery, so as to function as a BiPAP, an APAP, or a VPAP, or to obtain the information for executing/adjusting the ramp procedure. Identically, the BiPAP device, APAP device, or VPAP device also can obtain extra bases for further adjusting the air delivery. Thereby, the regulation of the air delivery behavior can be more accurate.

In addition, the type and the quantity of the sensor 22 connected to the sensing device 20 are also not restricted. The sensor 22 can be varied according to different patients' demands. Identically, the quantity of the sensing device 22 is not restrictive, and the PAP device can be implemented to connect with multiple sensing devices 22 at the same time.

It is important that in the present invention, the removable sensing device 20 provides the flexibility of information input. When different sensing devices 20 are connected, different respiratory/pressure characteristics can be obtained to provide different signal inputs, thereby offering the patient multiple choices.

It should be noticed normally the PAP device (CPAP, BiPAP, APAP, VPAP etc.) operates within a pressure range according to the settings, but with the confirmation of the doctor/technician, it is also possible that the sensing device can regulate the pressure limits as needed.

In the aforesaid, the air delivery system according to the present invention provides the patient the flexibility to decide the function of the PAP device through exchanging/increasing/decreasing the connected removable sensing device(s)/sensor(s), without being limited by the fixed hardware arrangement and air delivery behavior of the traditional PAP device. Therefore, the air delivery system of the present invention significantly improves the adaptation to different patients' demands. Furthermore, based on the architecture of the present invention, even a basic PAP device can function as an advanced APAP or BiPAP device by simply employing the removable sensing device. Thus, the customization can be achieved in a cost effective way.

The above examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is:

1. An air delivery system, comprising a PAP device and at least a removable sensing device, wherein:
the PAP device comprises:
a flow generator for providing breathable gas at a pressure elevated above atmosphere;
a patient interface, comprising:
a gas delivery tube coupled to the flow generator; and
a patient mask coupled to the gas delivery tube to receive breathable gas from the flow generator and to provide the gas, at a desired treatment pressure, to a patient's airway;
a processor for controlling a magnitude of the treatment pressure provided by the flow generator; and
a connector electrically connected to the removable sensing device; and
the removable sensing device, comprises:
at least a sensor for measuring a respiratory characteristic of the patient;
a front-end analog circuit for processing the measurements from the sensor to generate signal inputs to the processor; and
a connector electrically connected to the PAP device, wherein
the sensor is integrated with the patient interface, so as to measure the respiratory characteristic in a path between the patient's upper airway and the flow generator, and wherein
when the removable sensing device is separated from the PAP device, the PAP device enters a first operation mode, in which a preloaded program in the processor performs a first air delivery behavior to control the treatment pressure; and
when the removable sensing device is coupled to the PAP device through the connectors respectively thereof, the PAP device enters a second operation mode, in which the preloaded program performs a second air delivery behavior for adjusting the treatment pressure in accordance with the respiratory characteristic from the signal inputs.

2. The system as claimed in claim 1, wherein the sensor is placed on vent holes of the mask.

3. The system as claimed in claim 1, wherein the sensor is connected between the PAP device and the delivery tube.

4. The system as claimed in claim 3, wherein the sensor is connected to the PAP device via a further gas delivery tube.

5. The system as claimed in claim 1, wherein the sensor is at least one of a flow sensor or a thermal sensor.

6. The system as claimed in claim 1, wherein the removable sensing device further comprises a pressure sensor to measure the atmosphere under which the PAP device is located, and/or the pressure inside the patient mask or the gas delivery tube.

7. The system as claimed in claim 1, wherein the characteristic comprises a waveform contour of inspiratory and expiratory flow.

8. The system as claimed in claim 7, wherein the preloaded program, based on the waveform contour, determines the occurrence of an apnea/hypopnea, and/or the duration of an apnea/hypopnea.

9. The system as claimed in claim 1, wherein the front-end analog circuit provides one or more functions selected from a group consisting of: signal filtering, signal amplification, and level shifting.

10. The system as claimed in claim 1, wherein the removable sensing device further comprises an analog to digital converter.

11. The system as claimed in claim 1, wherein the adjustment of the treatment pressure is to have an increment or a decrement, or to remain the same.

12. The system as claimed in claim 1, wherein the number of the removable sensing device is implemented to be a plurality of sensing devices.

13. An air delivery system, comprising a PAP device and at least a removable sensing device, wherein:
the PAP device comprises:
a flow generator for providing breathable gas at a pressure elevated above atmosphere;
a patient interface, comprising:
a gas delivery tube coupled to the flow generator; and
a patient mask coupled to the gas delivery tube to receive breathable gas from the flow generator and to provide the gas, at a desired treatment pressure, to a patient's airway;
a processor for controlling a magnitude of the treatment pressure provided by the flow generator; and
a connector electrically connected to the removable sensing device; and
the removable sensing device, comprises:
a pressure sensor for measuring a pressure characteristic;
a front-end analog circuit for processing the characteristic from the pressure sensor to generate signal inputs to the processor; and
a connector electrically connected to the PAP device, wherein
the pressure sensor is integrated with the patient interface, so as to measure the pressure characteristic in a path between the patient's upper airway and the flow generator; and
wherein
when the removable sensing device is separated from the PAP device, the PAP device enters a first operation mode, in which a preloaded program in the processor performs a first air delivery behavior to control the treatment pressure; and
when the removable sensing device is coupled to the PAP device through the connectors respectively thereof, the PAP device enters a second operation mode, in which the preloaded program performs a second air delivery behavior for adjusting the treatment pressure in accordance with the pressure characteristic from the signal inputs.

14. The system as claimed in claim 13, wherein the pressure characteristic comprises a pressure variation caused by the patient's respiration.

15. The system as claimed in claim 13, wherein the pressure sensor is further implemented to measure the atmosphere under which the PAP device is located.

* * * * *